US008118855B2

(12) United States Patent
Hartley et al.

(10) Patent No.: US 8,118,855 B2
(45) Date of Patent: Feb. 21, 2012

(54) CURVE FORMING STENT GRAFT

(75) Inventors: David Ernest Hartley, Wannanup (AU);
Blayne A. Roeder, Lafayette, IN (US);
Werner D. Ducke, Greenwood (AU)

(73) Assignees: Cook Medical Technologies LLC,
Bloomington, IN (US); **William A.
Cook Australia Pty. Ltd.**, Queensland
(AU)

( * ) Notice: Subject to any disclaimer, the term of this patent is extended or adjusted under 35 U.S.C. 154(b) by 0 days.

(21) Appl. No.: 12/894,864

(22) Filed: Sep. 30, 2010

(65) Prior Publication Data

US 2011/0264192 A1 Oct. 27, 2011

(30) Foreign Application Priority Data

Apr. 23, 2010 (AU) .................................. 2010201676

(51) Int. Cl.
*A61F 2/86* (2006.01)
(52) U.S. Cl. ...................................... 623/1.12; 623/1.23
(58) Field of Classification Search .................. 623/1.12,
623/1.23, 1.28, 1.3
See application file for complete search history.

(56) References Cited

U.S. PATENT DOCUMENTS

| 4,902,508 | A | 2/1990 | Badylak et al. |
| 4,913,141 | A | 4/1990 | Hillstead |
| 5,711,969 | A | 1/1998 | Patel et al. |
| 5,733,337 | A | 3/1998 | Carr, Jr. et al. |
| 5,873,906 | A | 2/1999 | Lau et al. |
| 5,885,619 | A | 3/1999 | Patel et al. |
| 5,955,110 | A | 9/1999 | Patel et al. |
| 5,968,096 | A | 10/1999 | Whitson et al. |
| 6,346,118 | B1 * | 2/2002 | Baker et al. ................... 623/1.12 |
| 6,352,561 | B1 * | 3/2002 | Leopold et al. .............. 623/1.23 |
| 6,524,335 | B1 | 2/2003 | Hartley et al. |
| 6,974,471 | B2 | 12/2005 | Van Schie et al. |
| 7,758,626 | B2 * | 7/2010 | Kim et al. ..................... 623/1.11 |
| 2002/0040236 | A1 * | 4/2002 | Lau et al. ..................... 623/1.12 |

(Continued)

FOREIGN PATENT DOCUMENTS

EP 0664107 7/1995

(Continued)

OTHER PUBLICATIONS

Tam Huynh, Ginger Abraham, James Murray, Kelvin Brockbank, Per-Otto Hagen, Susan Sullivan, Remoldeling of an acellular collagen graft into a physiologically responsive neovessel, Nature Biotechnology, Nov. 1999, pp. 1083-1086, vol. 17.

*Primary Examiner* — Thomas J Sweet
*Assistant Examiner* — Cheryl Miller
(74) *Attorney, Agent, or Firm* — Richard J. Godlewski

(57) ABSTRACT

A curve forming stent graft for curved vessels such as the thoracic arch. The stent graft has a tubular body zig zag self expanding stents fastened to and supporting the tubular body. The zig zag self expanding stents comprising struts and points between adjacent struts thereby defining proximal end points and distal end points. A temporary diameter constriction arrangement associated with the least some of the plurality of zig zag self expanding stents comprises a pair of adjacent distal end points being releasably retained adjacent each other whereby at rest the tubular body of the stent graft is in a substantially sawtooth form and when released in a curved configuration a distal end point of a stent overlaps a proximal end point of a distally adjacent stent to facilitate curvature of the stent graft in a curved vessel.

12 Claims, 3 Drawing Sheets

U.S. PATENT DOCUMENTS

| | | | |
|---|---|---|---|
| 2002/0173837 A1* | 11/2002 | Lauterjung | 623/1.12 |
| 2004/0243221 A1* | 12/2004 | Fawzi et al. | 623/1.23 |
| 2007/0043425 A1 | 2/2007 | Hartley et al. | |
| 2007/0142896 A1 | 6/2007 | Anderson et al. | |
| 2008/0294234 A1 | 11/2008 | Hartley et al. | |
| 2009/0138072 A1* | 5/2009 | Gendreau | 623/1.15 |
| 2010/0114290 A1 | 5/2010 | Rasmussen et al. | |

FOREIGN PATENT DOCUMENTS

| | | |
|---|---|---|
| WO | 9822158 | 5/1998 |
| WO | 03/034948 A1 | 5/2003 |
| WO | 2008/051543 A2 | 5/2008 |
| WO | 2008140796 | 11/2008 |
| WO | 2010062362 A1 | 6/2010 |
| WO | PCT/US2010/050877 | 11/2010 |

\* cited by examiner

CURVE FORMING STENT GRAFT

TECHNICAL FIELD

This disclosure relates to a medical device and more particularly to a stent graft for mounting onto a deployment device for endovascular introduction into the vasculature of a patient.

BACKGROUND

This disclosure will be particularly discussed in relation to stent grafts for placement into the thoraco-abdominal aorta for the treatment of aneurysms and more specifically in relation to placement in a curved portion of the aorta such as the thoracic arch. The disclosure, however, is not so restricted and may be applied to stent grafts for placement in any lumen of the human or animal body.

A stent graft is in a constricted form when it is delivered by endoluminal techniques to a deployment site within such a curved portion of the aorta. There have been devised diameter reducing arrangements for stent grafts so that there is a partial release stage of the stent graft after a covering sheath has been withdrawn. At this stage, the stent graft has expanded in diameter to such an extent that the physician can visualise using radiographic techniques the position of the stent graft, while at the same time the stent graft can still be rotated and moved longitudinally to position the stent graft correctly. The diameter reducing arrangements can be subsequently released to allow the stent graft to fully expand engage the wall of the vessel to form an alternative flow path through the vessel to bypass an aneurysm, for instance.

The problem with a curved lumen with significant continuing blood flow and such a staged release arrangement is that the proximal or leading edge of the stent graft particularly at the inner side of the curved lumen may not engage against the wall of the lumen and may fold in thereby blocking the desired flow path and allowing bypass to continue into the aneurysm. It is also important that a strent graft take up the curvature of a vessel into which it is placed.

It is an object of this disclosure to provide a diameter reducing arrangement so that this problem can be reduced or to at least to provide a physician with an alternative arrangement.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

BRIEF DESCRIPTION OF THE INVENTION

In one form therefore the disclosure is said to reside in a stent graft comprising a tubular body of a biocompatible graft material and a plurality of zig zag self expanding stents fastened to and supporting the tubular body, the tubular body comprising a first end and a second end, at least some of the plurality of zig zag self expanding stents comprising struts and points between adjacent struts thereby defining first points and second points, the first points being nearer to the first end and the second points being nearer to the second end, and a temporary constriction arrangement associated with the at least some of the plurality of zig zag self expanding stents, the temporary constriction arrangement comprising at least one pair of adjacent second points being releasably retained adjacent each other.

Preferably the temporary constriction arrangement comprises a release filament and the second points being releasably retained to the release filament.

The release filament can be a wire such as a stainless steel or nitinol wire or can be a synthetic thread.

Preferably the releasable retention to the release filament comprises a flexible threads extending around the respective second points and around the release filament whereby withdrawal of the release filament releases the flexible threads and thereby the temporary constriction arrangement.

Preferably the release filament is engaged with the tubular body and the engagement of the release filament to the tubular body comprises the release filament being stitched into the biocompatible graft material of the tubular body longitudinally therealong and respective flexible threads extending around the respective second points are engaged around the release filament.

The flexible threads may be a suture material or similar material which is biocompatible. When the flexible thread is released it remain with the stent graft but on the outside of the stent graft and hence would not cause a problem for blood flow.

There can be two temporary constriction arrangements, the two temporary constriction arrangements being on opposite sides of the tubular body.

The two temporary constriction arrangements on opposite sides of the tubular body comprise separate release filaments, the separate release filaments being stitched into the biocompatible graft material of the tubular body longitudinally therealong on opposite sides of the tubular body.

The self expanding stents can comprise nitinol or stainless steel.

In an alternative form the disclosure comprises a curve forming stent graft comprising a tubular body of a biocompatible graft material and a plurality of zig zag self expanding stents fastened to and supporting the tubular body, the tubular body comprising a proximal end and a distal end, at least some of the plurality of zig zag self expanding stents comprising struts and points between adjacent struts thereby defining proximal end points and distal end points, the distal end points being nearer to the distal end of the tubular body and the proximal end points being nearer to the proximal end of the tubular body, and a temporary diameter constriction arrangement associated with the at least some of the plurality of zig zag self expanding stents, the temporary diameter constriction arrangement comprising at least adjacent distal end points of the least some of the plurality of zig zag self expanding stents being releasably retained adjacent each other whereby at rest the tubular body of the stent graft is in a substantially sawtooth form.

The self expanding stents can comprise nitinol or stainless steel. A nitinol stent may have for instance, 6 to 8 distal end points and an equal number of proximal end points. A stainless steel stent may have from 10 to 16 distal end points and an equal number of proximal end points.

In one embodiment the at least adjacent distal end points comprise immediately adjacent points and in an alternative embodiment the at least adjacent distal end points can comprise adjacent but one points. The former embodiment with immediately adjacent points is more useful where the stent is a nitinol stent because a nitinol stent usually has less points and pulling together the immediately adjacent points will give sufficient diameter reduction. The latter embodiment with adjacent but one points is more useful where the stent is a stainless steel stent because a stainless steel stent usually has more points and pulling together the adjacent but one points may be necessary give a sufficient diameter reduction.

Preferably the temporary diameter constriction arrangement comprises a release wire engaged into the tubular body between the at least adjacent distal end points, and the distal end points being releasably retained to the release wire.

Preferably the releasable retention to the release wire comprises a flexible threads extending around the respective distal end points and around the release wire whereby withdrawal of the release wire releases the flexible threads and thereby the temporary diameter constriction arrangement.

Preferably the engagement of the release wire to the tubular body comprises the release wire being stitched into the biocompatible graft material of the tubular body longitudinally therealong and respective flexible threads extending around the respective distal end points are engaged around the release wire.

Preferably the curve forming stent graft comprises two temporary constriction arrangements, the two temporary diameter constriction arrangements being on opposite sides of the tubular body.

Preferably the two temporary diameter constriction arrangements on opposite sides of the tubular body comprise separate release wires the separate releases wire being stitched into the biocompatible graft material of the tubular body longitudinally therealong on opposite sides of the tubular body.

In an alternative form the disclosure comprises a curve forming stent graft comprising a tubular body of a biocompatible graft material and a plurality of zig zag self expanding stents fastened to and supporting the tubular body, the tubular body comprising a proximal end and a distal end, the tubular body comprising diametrically opposed longitudinal walls intended to be inner curved and outer curved walls when the tubular body is placed into a curved lumen and diametrically opposed lateral longitudinal walls intended to be respective side walls when the tubular body is placed into the curved lumen; at least some of the plurality of zig zag self expanding stents comprising struts and points between adjacent struts thereby defining proximal end points and distal end points, the distal end points being nearer to the distal end of the tubular body and the proximal end points being nearer to the proximal end of the tubular body, and two temporary diameter constriction arrangements associated with the at least some of the plurality of zig zag self expanding stents, the temporary diameter constriction arrangement comprising a pair of adjacent distal points of the at least some of the plurality of zig zag self expanding stents along the diametrically opposed lateral longitudinal walls being releasably retained adjacent each other whereby at rest the tubular body of the stent graft is in a substantially sawtooth form along the respective intended to be inner curved and outer curved walls.

In an alternative form the disclosure comprises a curve forming stent graft comprising a tubular body of a biocompatible graft material and a plurality of zig zag self expanding stents fastened to and supporting the tubular body, the tubular body comprising a proximal end and a distal end, the tubular body comprising diametrically opposed longitudinal walls intended to be inner curved and outer curved walls when the tubular body is placed into a curved lumen and diametrically opposed lateral longitudinal walls intended to be respective side walls when the tubular body is placed into the curved lumen; at least some of the plurality of zig zag self expanding stents comprising struts and points between adjacent struts thereby defining proximal end points and distal end points, the distal end points being nearer to the distal end of the tubular body and the proximal end points being nearer to the proximal end of the tubular body, and two temporary diameter constriction arrangements associated with the at least some of the plurality of zig zag self expanding stents, the temporary diameter constriction arrangement comprising a pair of adjacent distal points of the least some of the plurality of zig zag self expanding stents along the diametrically opposed lateral longitudinal walls being releasably retained adjacent each other, the temporary diameter constriction arrangements each comprises a release wire engaged into the tubular body between the pair of adjacent distal end points, and each of the pair of adjacent distal end points being releasably retained to the release wire, the engagement of the release wire to the tubular body comprising the release wire being stitched into the biocompatible graft material of the tubular body longitudinally therealong and the releasable retention to the release wire comprises a flexible threads extending around the respective distal end points and around the release wire whereby withdrawal of the release wire releases the flexible threads and thereby the temporary diameter constriction arrangement, whereby at rest the tubular body of the stent graft is in a substantially sawtooth form along the respective intended to be inner curved and outer curved walls and when in a curved configuration a distal end point of a stent overlaps a proximal end point of a distally adjacent stent to facilitate curvature of the stent graft in a curved vessel.

Preferably the least some of the plurality of zig zag self expanding stents include a proximal-most self expanding zig zag stent.

BRIEF DESCRIPTION OF THE DRAWINGS

This then generally describes the disclosure but to assist with understanding reference will now be made to drawings which show preferred embodiments of the disclosure.

In the drawings.

DISCUSSION OF PREFERRED EMBODIMENTS

Figure 1:
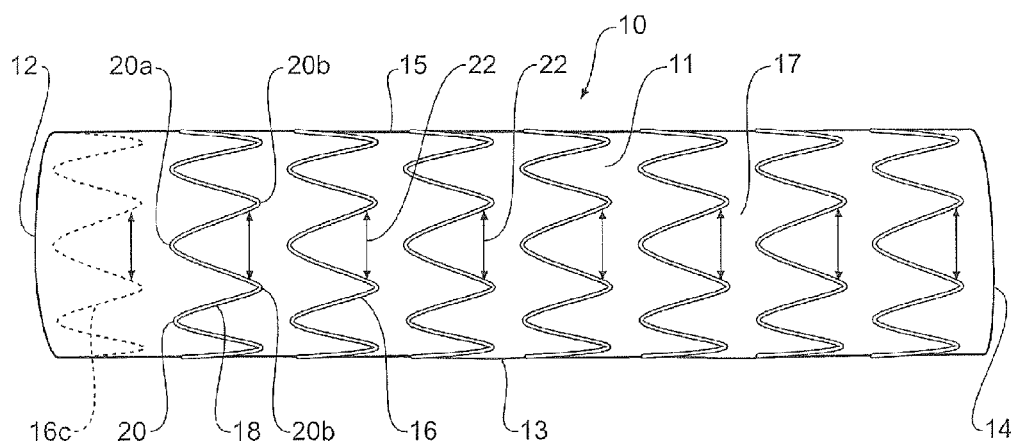
FIG. 1 shows a stent graft according to an embodiment of the disclosure and showing the position for placement of the temporary constriction arrangements.

In the drawings a stent graft 10 comprises a tubular body of a biocompatible graft material 11. The tubular body has a first or proximal end 12 and a second or distal end 14. The stent graft has an inner curve side 13 which is the side which when the stent graft is deployed into a curved lumen is intended to be on the inside of the curve. The stent graft has an outer curve side 15 which is the side which when the stent graft is deployed into a curved lumen is intended to be on the outside of the curve. In between the inner and outer sides 13 and 15 is a lateral longitudinal side 17. A corresponding lateral longitudinal side is on the other side of the stent graft.

The stent graft is supported by a plurality of self expanding Gianturco style zig zag stents 16. Each stent 16 comprises a plurality of struts 18 and points 20 between adjacent struts and each stent is continuous around the tubular body. The points 20 comprise first end or proximal end points 20a and second end or distal end points 20b.

The tubular graft material can include polytetrafluoroethylene, dacron, polyamide or any other suitable biocompatible graft material.

While DACRON, expanded polytetrafluoroethylene (ePTFE), or other synthetic biocompatible materials can be used for the tubular graft material for the stent graft, a naturally occurring biomaterial, such as collagen, is highly desirable, particularly a specially derived collagen material known as an extracellular matrix (ECM), such as small intestinal submucosa (SIS). Besides SIS, examples of ECM's include pericardium, stomach submucosa, liver basement membrane, urinary bladder submucosa, tissue mucosa, and dura mater.

SIS is particularly useful, and can be made in the fashion described in Badylak et al., U.S. Pat. No. 4,902,508; Intestinal Collagen Layer described in U.S. Pat. No. 5,733,337 to Carr and in 17 Nature Biotechnology 1083 (November 1999); Cook et al., WIPO Publication WO 98/22158, dated 28 May 1998, which is the published application of PCT/US97/14855, the teachings of which are incorporated herein by reference. Irrespective of the origin of the material (synthetic versus naturally occurring), the material can be made thicker by making multilaminate constructs, for example SIS constructs as described in U.S. Pat. Nos. 5,968,096; 5,955,110; 5,885,619; and 5,711,969. In addition to xenogenic biomaterials, such as SIS, autologous tissue can be harvested as well, for use in forming the tubular graft material. Additionally Elastin or Elastin-Like Polypetides (ELPs) and the like offer potential as a material to fabricate the tubular graft material to form a device with exceptional biocompatibility. SIS is available from Cook Biotech, West Lafayette, Ind., USA.

Various stent types and stent constructions may be used in the stent-graft of the present invention. In general, the stents may be formed from any material and have any structure that is self expanding and has sufficient radial strength to retain its shape. Self-expanding stents include those that have a spring-like action which causes the stent to radially expand, or stents which expand due to the memory properties of the stent material for a particular configuration at a certain temperature. A preferred self-expanding stent is the Z-STENT®, available from Cook, Incorporated, Bloomington, Ind., USA.

Any suitable stent material is contemplated including, but not limited to, stainless steel, platinum, gold, titanium, Nitinol™ and other nickel-titanium alloys, MP35N® and other nickel-cobalt alloys, Cobalt L-605™ and other cobalt-chromium alloys, other biocompatible metals, metal-alloys, as well as polymeric stents.

The stents 16 can be affixed to the biocompatible graft material 12 by being stitched to the graft material by use of a suture thread or other suitable fibre, or by an adhesive. The adhesive can be applied all over or in longitudinal or other direction strips onto the biocompatible graft material 12. The polymer adhesive may be a urethane adhesive such as Thoralon™ (sold by Cook Incorporated, Bloomington, Ind., USA). The adhesive can be sprayed or painted on.

In FIG. 1 the arrows 22 show the region in which the temporary constriction arrangements are applied so as to draw together in a releasable manner adjacent second or distal end points 20b on each stent 16 along the length of the stent graft 10.

Figure 2:
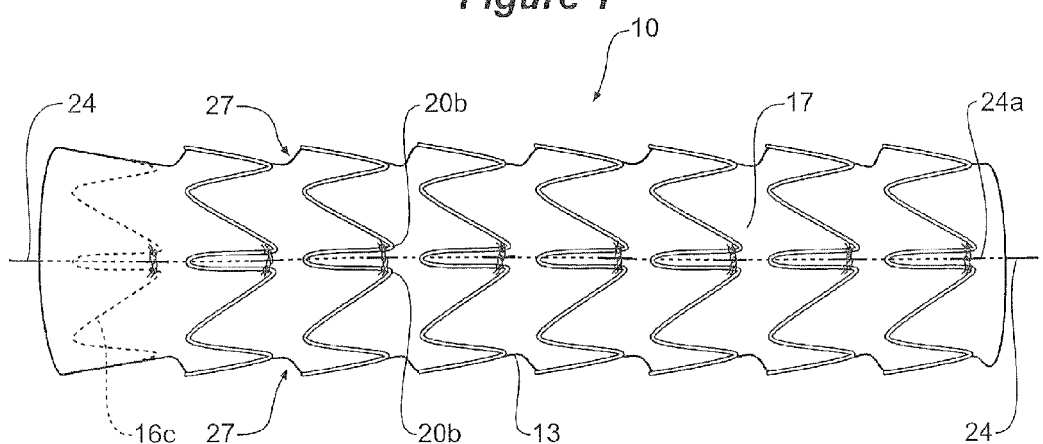
FIG. 2 shows the embodiment of FIG. 1 with the temporary constriction arrangements in place and showing the "sawtooth effect" on both sides of the stent graft.
Figure 3:
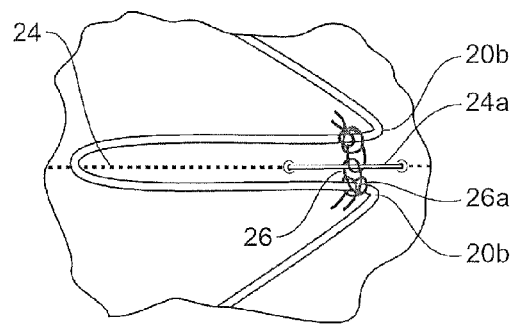
FIG. 3 shows detail of one embodiment of a temporary constriction arrangement according to the present disclosure.

FIG. 2 shows the application of the temporary constriction arrangements and FIG. 3 shows detail of a temporary constriction arrangement. A release wire 24 is stitched through the graft material longitudinally at the lateral longitudinal side 17. At a region between two adjacent second or distal end points 20b the release wire 24 is outside the graft material as an exposed portion 24a of the stitched release wire 24. A suture thread or similar flexible material 26 is passed around the exposed portion 24a of the stitched release wire 24 and around the adjacent second or distal end point 20b and tightened up and knotted as at 26a on either side of the release wire 24. This has the effect of drawing the two adjacent second or distal end points of the stent 16 together and therefore the draws in adjacent struts of the stent and the attached graft material at the top and bottom of the stent graft to give a "sawtooth effect" 27 when the stent graft is viewed in side profile as can be particularly seen in FIG. 2.

The proximal-most stent 16c is inside the graft material to give a smooth outside surface to enable sealing against the wall of a vessel into which the stent graft is deployed. The suture threads are stitched through the graft material to engage the distal end point of the stent to give the temporary constriction arrangement.

Figure 4:
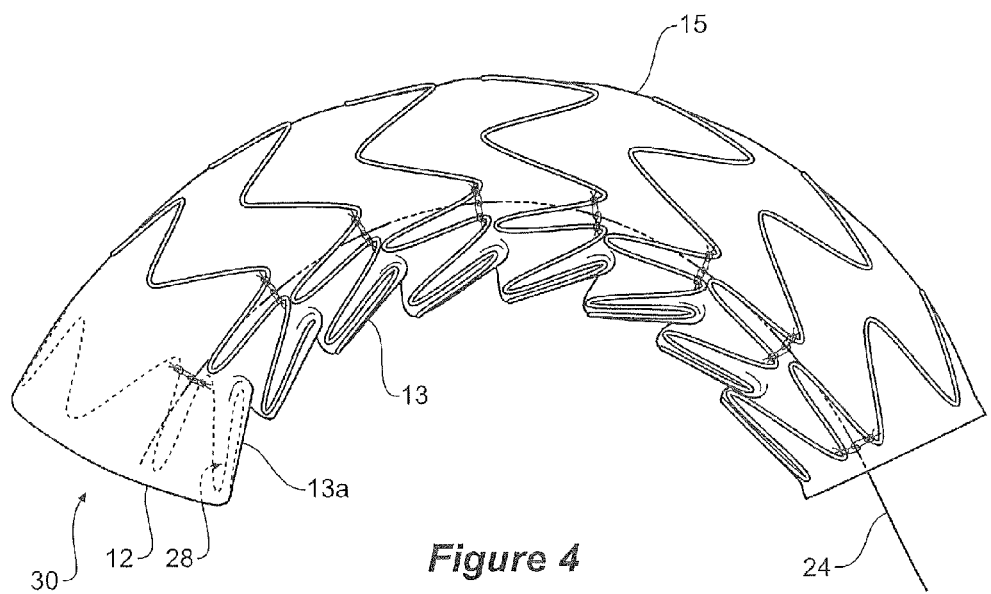
FIG. 4 shows the embodiment of FIG. 1 with the temporary constriction arrangements in place and the stent graft curved to show a greater "sawtooth effect" on an inner curved side of the stent graft.

When the stent graft is placed into a longitudinally curved shape, as is shown in FIG. 4, the "sawtooth effect" when the stent graft is viewed in side profile disappears on the outer curved side 15 which is the side which, when the stent graft is deployed into a curved lumen, is intended to be on the outside of the curve and is more accentuated on the inner curved side 13 which is the side which, when the stent graft is deployed into a curved lumen, is intended to be on the inside of the curve.

Figure 5:
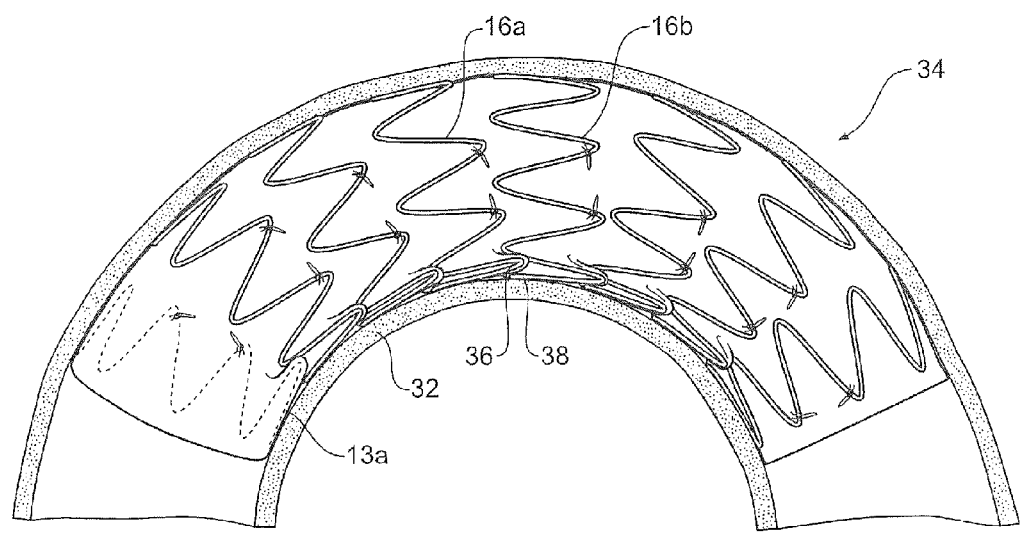
FIG. 5 shows the embodiment of FIG. 1 with the temporary constriction arrangements released and the stent graft deployed in a curved lumen to show the overlapped stents on an inner curved side of the stent graft.

As shown in FIG. 4 the stent graft is still in its temporarily constricted state. It can be particularly noted that at the proximal end 12 of the stent graft the apparent diameter is greater than the diameter at about one stent distance back from the proximal end. This configuration means that inside the tubular body and angled internal face 28 is presented to the flow of blood as indicated by the arrow 30 so that when the temporary constriction arrangement is released as shown in FIG. 5 the region 13a of the inner wall 13 will tend to be pushed towards the inner wall 32 of the curved vessel 34. The action will assist with correct placement of the stent graft against the wall of a vessel and assist in preventing the formation of a "parrot's beak" type of buckling of the proximal end of the stent graft which could cause partial blockage of the blood vessel during deployment of the stent graft.

FIG. 5 also shows that at the inner side 32 of the curved vessel 34 a distal or second end point 36 of a stent 16a overlaps a proximal end point 38 of a distally adjacent stent 16b to facilitate curvature and fitting of the stent graft in the curved vessel.

Figure 6:
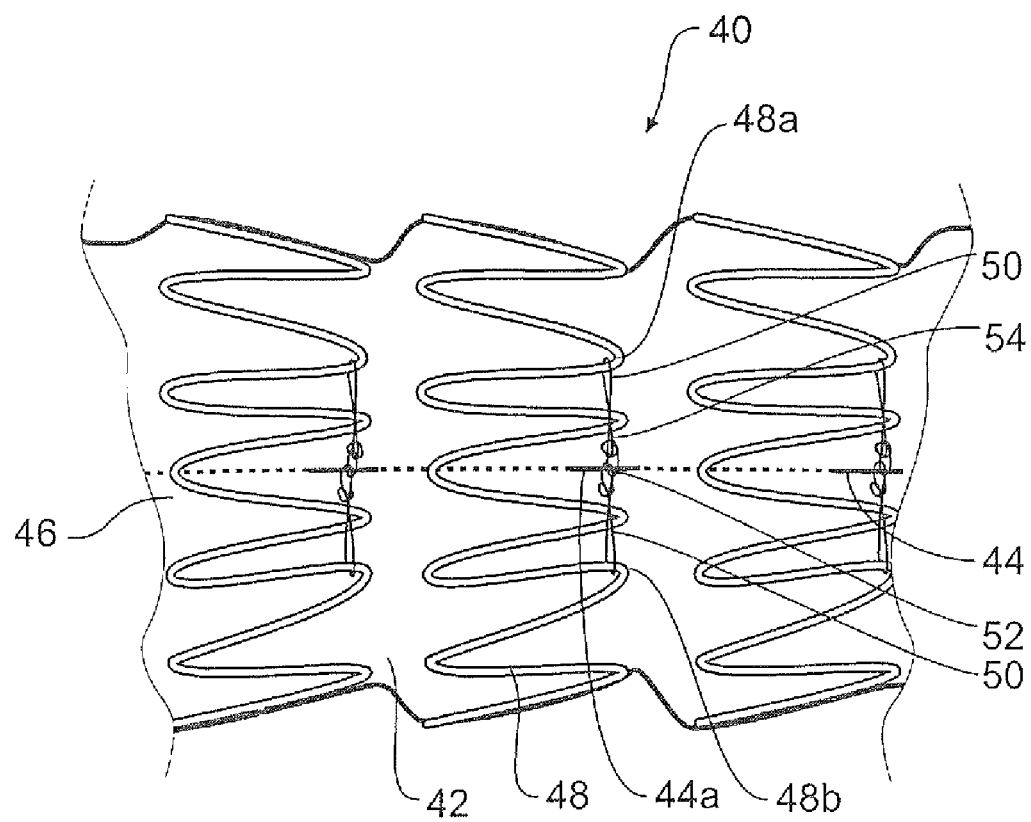
FIG. 6 shows detail of an alternative embodiment of a temporary constriction arrangement according to the present disclosure.

FIG. 6 shows detail of an alternative embodiment of a temporary constriction arrangement according to the present disclosure. In this embodiment the temporary restriction arrangement comprises a release wire 44 stitched through the graft material 42 of a stent graft 40 longitudinally at the lateral longitudinal side 46. At a region between two second or distal end points 48a and 48b of a stent 48 the release wire 44 is outside the graft material as an exposed portion 44a of the stitched release wire 44. A suture thread or similar flexible material 50 is passed around the exposed portion 44a of the stitched release wire 44 and around the second or distal end point 48b and tightened up and knotted as at 52. Similarly on the other side of the release wire 44 a suture thread or similar flexible material 50 is passed around the exposed portion 44a of the stitched release wire 44 and around the second or distal end point 48a and tightened up and knotted as at 54. This has the effect of drawing the two second or distal end points 48a and 48b of the stent 48 together and therefore the draws in the graft material at the top and bottom of the stent graft to give a "sawtooth effect". It will be noted that in this embodiment the adjacent but one end points are drawn together.

This embodiment with adjacent but one points being drawn together is more useful where the stent is a stainless steel stent because a stainless steel stent usually has more points and pulling together the adjacent but one points may be necessary give a sufficient diameter reduction.

Throughout this specification various indications have been given as to the scope of the invention but the invention is not limited to any one of these but may reside in two or more of these combined together. The examples are given for illustration only and not for limitation.

What is claimed is:

1. A stent graft comprising a tubular body of a biocompatible graft material and a plurality of zig zag self expanding stents fastened to and supporting the tubular body so as to form a plurality of stented regions separated by non-stented regions, the tubular body comprising a first end and a second end, at least some of the plurality of zig zag self expanding stents each comprising stent struts and stent bends between adjacent stent struts thereby defining first stent bends and second stent bends, the first stent bends being nearer to the first end of the tubular body and the second stent bends being nearer to the second end of the tubular body, and a temporary constriction arrangement associated with the at least some of the plurality of zig zag self expanding stents, the temporary constriction arrangement comprising at least adjacent second stent bends being releasably held circumferentially towards each other by respective flexible threads extending around and engaged to the respective second stent bends and around a release filament, the release filament being engaged with the tubular body by being stitched into the biocompatible graft material of the tubular body longitudinally therealong, the temporary constriction arrangement tapering at least some of the stented regions in a direction towards the second end of the tubular body while also tapering at least some of the non-stented regions in a direction different to the direction towards the second end, thereby creating a sawtooth effect in a longitudinal direction, whereby withdrawal of the release filament releases the flexible threads and thereby the temporary constriction arrangement.

2. A stent graft as in claim 1 wherein the temporary constriction arrangement comprises two temporary constriction arrangements, the two temporary constriction arrangements being on opposite sides of the tubular body and wherein the release filament comprises two separate release filaments being stitched into the biocompatible graft material of the tubular body longitudinally therealong on opposite sides of the tubular body.

3. A stent graft as in claim 1 wherein the self expanding stents comprise nitinol or stainless steel.

4. A curve forming stent graft comprising a tubular body of a biocompatible graft material and a plurality of zig zag self expanding stents fastened to and supporting the tubular body so as to form a plurality of stented regions separated by non-stented regions, the tubular body comprising a proximal end and a distal end, at least some of the plurality of zig zag self expanding stents each comprising stent struts and stent bends between adjacent stent struts thereby defining proximal end stent bends and distal end stent bends, the distal end stent bends being nearer to the distal end of the tubular body and the proximal end stent bends being nearer to the proximal end of the tubular body, and a temporary localized diameter constriction arrangement associated with the at least some of the plurality of zig zag self expanding stents, the temporary localized diameter constriction arrangement comprising adjacent distal end stent bends of the least some of the plurality of zig zag self expanding stents being releasably retained adjacent each other by respective flexible threads extending around the respective distal end stent bends and around a release wire whereby withdrawal of the release wire releases the flexible threads and thereby the temporary constriction arrangement and wherein the release wire is engaged to the tubular body by the release wire being stitched into the biocompatible graft material of the tubular body longitudinally therealong, the temporary constriction arrangement tapering at least some of the stented regions in a direction towards the distal end of the tubular body while also tapering at least some of the non-stented regions in a direction different to the direction towards the distal end, thereby creating a sawtooth effect in a longitudinal direction.

5. A curve forming stent graft as in claim 4 wherein the temporary constriction arrangement comprises two temporary constriction arrangements, the two temporary constriction arrangements being on opposite sides of the tubular body and wherein the release wire comprises two separate release wires being stitched into the biocompatible graft material of the tubular body longitudinally therealong on opposite sides of the tubular body.

6. A curve forming stent graft as in claim 5 wherein the adjacent distal end stent bends comprise immediately adjacent stent bends.

7. A curve forming stent graft as in claim 5 wherein the adjacent end stent bends comprise stent bends spaced apart by at least one further stent bend.

8. A curve forming stent graft comprising a tubular body of a biocompatible graft material and a plurality of zig zag self expanding stents fastened to and supporting the tubular body so as to form a plurality of stented regions separated by non-stented regions, the tubular body comprising a proximal end and a distal end, the tubular body comprising diametrically opposed longitudinal walls intended to be inner curved and outer curved walls when the tubular body is placed into a curved lumen and diametrically opposed lateral longitudinal walls intended to be respective side walls when the tubular body is placed into the curved lumen, at least some of the plurality of zig zag self expanding stents comprising stent struts and stent bends between adjacent stent struts thereby defining proximal end stent bends and distal end stent bends, the distal end stent bends being nearer to the distal end of the tubular body and the proximal end stent bends being nearer to the proximal end of the tubular body, and two temporary diameter constriction arrangements associated with the at least some of the plurality of zig zag self expanding stents, each of the temporary diameter constriction arrangements comprising a pair of adjacent distal stent bends of the least some of the plurality of zig zag self expanding stents along one of the diametrically opposed lateral longitudinal walls being releasably retained adjacent each other by respective flexible threads extending around the respective distal end stent bends and around a release wire engaged into the tubular body between the pair of adjacent distal end stent bends, the two temporary constriction arrangements tapering at least some of the stented regions in a direction towards the distal end of the tubular body while also tapering at least some of the non-stented regions in a direction different to the direction towards the distal end, thereby creating a sawtooth effect in a longitudinal direction, whereby withdrawal of each of the release wires releases the flexible threads and thereby the two temporary constriction arrangements, the release wires being stitched into the biocompatible graft material of the tubular body longitudinally therealong, whereby at rest the tubular body of the stent graft is in a substantially sawtooth form along the respective longitudinal walls intended to be inner curved and outer curved walls.

9. A curve forming stent graft as in claim 8 wherein the two temporary diameter constriction arrangements are on opposite sides of the tubular body.

10. A curve forming stent graft as in claim 9 wherein each of the release wires are stitched into the biocompatible graft material of the tubular body longitudinally therealong on opposite sides of the tubular body.

11. A curve forming stent graft comprising a tubular body of a biocompatible graft material and a plurality of zig zag self expanding stents fastened to and supporting the tubular body so as to form a plurality of stented regions separated by non-stented regions, the tubular body comprising a proximal end and a distal end, the tubular body comprising diametrically opposed longitudinal walls intended to be inner curved and outer curved walls when the tubular body is placed into a curved lumen and diametrically opposed lateral longitudinal walls intended to be respective side walls when the tubular body is placed into the curved lumen; at least some of the plurality of zig zag self expanding stents each comprising stent struts and stent bends between adjacent stent struts thereby defining proximal end stent bends and distal end stent bends, the distal end stent bends being nearer to the distal end of the tubular body and the proximal end stent bends being nearer to the proximal end of the tubular body, and two temporary diameter constriction arrangements associated with the at least some of the plurality of zig zag self expanding stents, each of the two temporary diameter constriction arrangements comprising a pair of adjacent distal stent bends of the least some of the plurality of zig zag self expanding stents along one of the diametrically opposed lateral longitudinal walls being releasably retained adjacent each other, the two temporary diameter constriction arrangements each comprising a release wire engaged into the tubular body between the pair of adjacent distal end stent bends, and each of the pair of adjacent distal end stent bends being releasably retained to the respective release wire, engagement of each of the release wire to the tubular body comprising the release wires being stitched into the biocompatible graft material of the tubular body longitudinally therealong and the releasable retention to the respective release wire comprises flexible threads extending around the respective distal end stent bends and around the release wire, the two temporary constriction arrangements tapering at least some of the stented regions in a direction towards the distal end of the tubular body while also tapering at least some of the non-stented regions in a direction different to the direction towards the distal end, thereby creating a sawtooth effect in a longitudinal direction, whereby withdrawal of the release wires releases the flexible threads and thereby the temporary diameter constriction arrangements, whereby at rest the tubular body of the stent graft is in a substantially sawtooth form along the respective intended to be inner curved and outer curved walls and when in a curved configuration a distal end stent bend of a stent overlaps a proximal end stent bend of a distally adjacent stent to facilitate curvature of the stent graft in a curved vessel.

12. A curve forming stent graft as in claim 11 wherein the least some of the plurality of zig zag self expanding stents comprises a proximal-most self expanding zig zag stent.

* * * * *